US005512592A

United States Patent [19]
Zaloga et al.

[11] Patent Number: 5,512,592
[45] Date of Patent: Apr. 30, 1996

[54] METHOD OF PRODUCING CARDIOTONIC EFFECT AND IMPROVING CARDIAC CONTRACTILE FUNCTION BY ADMINISTRATION OF CARNOSINE

[75] Inventors: Gary P. Zaloga; Pamela Roberts, both of Winston-Salem, N.C.

[73] Assignee: Wake Forest University, Winston-Salem, N.C.

[21] Appl. No.: 303,455

[22] Filed: Sep. 9, 1994

[51] Int. Cl.$^6$ .................................................. A61K 31/415
[52] U.S. Cl. ........................................................ 514/400
[58] Field of Search ............................................ 514/400

[56] References Cited

U.S. PATENT DOCUMENTS

| | | | |
|---|---|---|---|
| 4,059,694 | 11/1977 | Norton et al. | 424/177 |
| 4,103,004 | 7/1978 | Norton et al. | 424/177 |
| 4,166,113 | 8/1979 | Norton et al. | 424/177 |
| 4,219,549 | 8/1980 | Jarreau et al. | 424/241 |
| 4,400,371 | 8/1983 | De Felice | 424/10 |
| 4,751,284 | 6/1988 | Forssmann | 530/329 |
| 4,975,444 | 12/1990 | Danilewicz et al. | 514/354 |
| 5,122,596 | 6/1992 | Phillips et al. | 530/350 |
| 5,250,517 | 10/1993 | Branca et al. | 514/18 |

OTHER PUBLICATIONS

D. Fitzpatrick et al., Proceedings of the Society for Experimental Biology and Medicine, 165: 404–408 (1980).
J.-M. Arnould et al., Archives Internationales de Physiologie et de Biochimie, 85: 339–350 (1977).
S. M. Harrison et al., Physiological Society, p. 197P, Sep. 1985.
B. Cianciaruso et al., Am. J. Physiol., 248: E51–E57 (1985).
J. Fitzpatrick et al., Nephron, 59: 299–303 (1991).
S. Snyder, Science, 209: 976–983 (1980).
F. Sadikali et al., Gut, 16: 585–589 (1975).
M. Otsuka et al., Peptide Neurotransmitters, pp. 425–439, (1978).
W. Nutzenadel et al., American Journal of Physiology, 230: 643–651 (1976).
A. Neidle et al., Brain Research 80: 359–364 (1974).
P. Johnson et al., Biochemical and Biophysical Research Communications, 109: 769–775 (1982).
T. Hama et al., J. Nutr. Sci. Vitaminol., 22: 147–157 (1976).
L. Fleisher et al., Pediatric Res., 14: 269–271 (1980).
V. Ganapathy et al., The Journal of Biological Chemistry, 258: 14189–14192 (1983).
V. Ganapathy et al., Biochimica et Biophysica Acta, 691: 362–366 (1982).
D. Fisher et al., Proceedings of the Society for Experimental Biology and Medicine, 158: 402–405 (1978).
D. Brotman et al., Critical Care Medicine, 18: 317–321 (1990).
CA 117:67392, Lamont et al., 1992.

*Primary Examiner*—Kimberly Jordan
*Attorney, Agent, or Firm*—Dann, Dorfman, Herrell and Skillman

[57] ABSTRACT

The invention provides a method of producing a cardiotonic effect by administration of carnosine (N-β-Alanyl-L-histidine) or its pharmaceutically acceptable salt in an amount sufficient to produce such effect.

12 Claims, No Drawings

METHOD OF PRODUCING CARDIOTONIC EFFECT AND IMPROVING CARDIAC CONTRACTILE FUNCTION BY ADMINISTRATION OF CARNOSINE

THE FIELD OF THE INVENTION

The present invention relates to the use of carnosine for the treatment of cardiac insufficiency.

DESCRIPTION OF THE PRIOR ART

Cardiac insufficiency commonly results from impaired muscle contraction. Cardiac contraction is impaired in many disease states, including congestive heart failure, myocardial infarction, sepsis and trauma. Cardiac contractile impairment can also occur during major operations, which may directly or indirectly involve the heart, e.g., vascular surgery or cardiac bypass surgery.

Current pharmacologic support of impaired cardiac contraction typically involves the following:

1. Drugs which stimulate cardiac beta-adrenergic receptors (e.g., isoproterenol, epinephrine, norepinephrine, dobutamine, dopamine);
2. Drugs which inhibit phosphodiesterase enzymes (e.g., amrinone, milrinone);
3. Drugs which block the sodium-potassium ATPase enzyme (e.g., Digoxin); and
4. Drugs (e.g., nitrates, angiotensin converting enzyme inhibitors, hydralazine) which reduce the pressure the heart contracts against (i.e., afterload). These drugs also improve cardiac contraction by improving cardiac compliance;
5. Agents which have direct cardiac effects (not mediated via receptors) (e.g., calcium).

Beta-adrenergic receptor agonists are the most commonly used drugs for support of the cardiovascular system in critically ill or postoperative patients. These drugs stimulate the production of cyclic adenosine monophosphate (cAMP) and increase calcium entry into myocytes, improving contraction. Beta-receptor agonists also stimulate chronotropic responses in the heart and may cause undesirable increases in heart rate or arrhythmias. These effects frequently limit their usefulness. Some beta-adrenergic agonists (e.g., epinephrine, norepinephrine, dopamine) also stimulate alpha-adrenergic receptors and may result in undesirable increases in cardiac afterload or decreased organ blood flow (due to vasoconstriction). Loss of drug responsiveness, so called "down regulation" or "resistance", is a frequent problem with beta-adrenergic agonists in both acute and chronic cardiac insufficiency.

Drugs which inhibit phosphodiesterase enzymes, such as amrinone and milrinone, elevate cAMP in the heart by impairing its degradation. These agents have not yet proved to be superior to beta-adrenergic agents and many patients respond minimally to such drugs.

Sodium-potassium ATPase inhibitors, such as digoxin, cause sodium to accumulate in the cardiac cell. The sodium is subsequently exchanged for calcium, improving cardiac contraction. These drugs are long acting and lack the potency of beta-adrenergic agonists. They also predispose to arrhythmias.

Afterload reducing agents improve cardiac output by decreasing the pressure the heart must pump against. A major side effect from these agents is hypotension. Furthermore, these agents are poorly tolerated in the severely compromised patient with minimal cardiac reserve or low blood pressure. While calcium has been shown to be essential for cardiac contraction, many studies indicate that calcium improves cardiac output minimally. Calcium has also been linked to myocardial damage during ischemia.

Although there exist a number of agents for cardiac support, many patients fail to respond to current agents adequately and most are associated with undesirable side effects. No agent has proved dependable under all circumstances. Thus, new cardiotonic agents with different mechanisms of action are continuously being sought.

Carnosine ($C_9H_{14}N_4O_3$), also known as N-β-Alanyl-L-histidine, is a dipeptide composed of the amino acids beta-alanine and histidine. Carnosine represents a large portion of mammalian intracellular nitrogen stores and serves as a reservoir for histidine which is available for histamine synthesis during stress. Carnosine has been found in mammalian cardiac and skeletal muscle tissue. Cardiac stores of carnosine are depleted in stressed (e.g., fracture, infected) animals. Stressed states (e.g., sepsis) are associated with diminished cardiac contraction. Carcinine (β-alanyl-histamine), a metabolite of carnosine, has also been found in cardiac tissue. Both of these peptides may be metabolized to histamine.

Histamine is present in high concentrations in cardiac muscle and is known to have effects upon the heart. Positive inotropic effects of histamine are mediated via H2 receptors while negative inotropic effects of histamine are mediated via H1 receptors. Undesirable effects of systemic administration of histamine include hypotension, positive chronotropic activity, slowing of atrioventricular conduction, enhanced ventricular automaticity, lowering of the fibrillation threshold, and coronary vasoconstriction. As a result, histamine has not been developed as an agent for cardiac support.

The function of carnosine and carcinine in normal physiology remains largely unknown. However, the presence of these peptides in cardiac tissue raises the possibility that they somehow participate in the maintenance of cardiac function. Recently, Brotman et al. (Critical Care Medicine, 18 (3): 317–21 (1990)) investigated the effects of carcinine and carnosine on the mammalian heart. Studies were carried out in the isolated perfused guinea pig heart, using doses of carcinine ranging from 10–100 micrograms and carnosine ranging from 10–300 micrograms. Although carcinine was found to exert a positive, dose-dependent inotropic effect, no detectable cardiac effect was reported for carnosine.

It has also been found that carcinine causes hypotension when administered intravenously to rabbits and rats. This effect limits its usefulness as a systemic agent.

Carnosine has been reported to accelerate wound healing, presumably via the release of histidine and stimulation of histamine synthesis. It has also been found that carnosine improves tensile strength and increases collagen deposition following exogenous carnosine administration (intradermal) to wounded rats treated with hydrocortisone and other chemotherapeutic agents.

Insofar as is known, carnosine has not previously been reported to be useful as a cardiotonic agent.

SUMMARY OF THE INVENTION

In accordance with the present invention, there is provided a method of producing a cardiotonic effect in a patient in need of such effect, which comprises administering to the patient the compound carnosine or its pharmaceutically acceptable salt in an amount effective to produce the desired effect. In addition to enhancing cardiac contractile function, carnosine has been found to stimulate heart rate (and cardiac oxygen demand) less than many currently available cardiotonic agents and, it appears, does not cause significant vasoconstriction. Carnosine may also have anti-arrhythmic and anti-ischemic effects, as well.

According to another aspect of this invention, a method for prolonging the survival of a patient suffering from cardiac insufficiency is provided which involves administering to the patient the compound carnosine or its pharmaceutically acceptable salt in an amount effective to improve cardiac contractile function in the recipient.

In carrying out the methods of the invention, carnosine may be administered in conjunction with a β-adrenergic receptor agonist or a phosphodiesterase inhibitor in an amount sufficient to produce a therapeutically effective increase in myocardial cyclic adenosine monophosphate (cAMP) levels.

For improving cardiac contractile function, carnosine and its pharmaceutically acceptable salts may be administered either enterally or parenterally.

DETAILED DESCRIPTION OF THE INVENTION

The beneficial cardiotonic effect of carnosine has been observed in animal studies, as will appear from the examples set forth below. Carnosine has been found to have potent inotropic activity in the isolated rat heart. Its potency equals or exceeds that of epinephrine or isoproterenol. Carnosine has also been found to possess chronotropic activity. Its chronotropic activity is less than that of epinephrine or isoproterenol. The inotropic activity of carnosine is not antagonized by β-adrenergic receptor blockade with propranolol or histamine-2 receptor (H2) blockade with cimetidine. Moreover, unlike epinephrine, carnosine does not stimulate the production of cAMP in isolated myocardial cells.

The experimental results indicate that carnosine is a new inotropic/chronotropic agent which mediates its cardiotonic activity through mechanisms separate from β-adrenergic and H2 receptors, and cAMP elevation. Carnosine thus appears to offer distinct advantages over currently available cardiotonic agents.

Carnosine or its pharmaceutically acceptable salts may be conveniently formulated for administration with a biologically acceptable excipient, such as water, buffered saline, polyol (for example, glycerol, propylene glycol, liquid polyethylene glycol and the like), suitable mixtures thereof and vegetable oil. The concentration of carnosine in the selected liquid excipient should normally be from about 1 mg/ml to about 100 mg/ml. Where appropriate, the action of contaminating microorganisms can be prevented by various anti-bacterial and anti-fungal agents, such as parabens, chlorobutanol, phenol, sorbic acid, thimerosal and the like. It will often be preferable to include isotonic agents, for example, glucose or sodium chloride.

As used herein, the term "pharmaceutically acceptable excipient" includes any and all carriers, solvents, dispersion media, coatings, anti-bacterial and anti-fungal agents, isotonic and adsorption delaying agents, components of nutritional support and the like. The use of such media and agents with pharmaceutically acceptable substances is known in the art. Except insofar as any conventional media or agent is incompatible with carnosine, its use in practicing the methods of the present invention is contemplated.

Carnosine may also be administered in accordance with the present invention as a component of a nutritional product, if desired.

Supplementary active ingredients, such as β-adrenergic receptor agonists, e.g., epinephrine, isoproterenol and dobutamine, or phosphodiesterase inhibitors, e.g., amrinone and milrinone, can also be administered in conjunction with carnosine, if necessary or desirable.

It is especially advantageous to formulate pharmaceutical preparations containing carnosine in dosage unit form for ease of administration and uniformity of dosage. Dosage unit form as used herein refers to a physically discrete unit of the pharmaceutical preparation appropriate for the patient undergoing treatment. Each dosage should contain a quantity of carnosine calculated to produce the desired cardiotonic effect in association with the selected pharmaceutical excipient. Procedures for determining the appropriate dosage unit are within the capabilities of those of ordinary skill in the art. The dose to be administered in a particular case must, of course, be determined on the basis of the age, weight and condition of the patient. An improvement in cardiac contractile function can be observed at doses in the range of about 0.01–0.4 gms/kg/day, the preferred range being from about 0.01 to about 0.1 gms/kg/day.

In carrying out the method of the invention, carnosine may be administered parenterally, e.g., intravenously, intraperitoneally, intramuscularly, subcutaneously or transdermally. Enteral administration of carnosine may also produce the desired cardiotonic effect. Intestinal absorption of small di- and tri-peptides is well known. Furthermore, intact adsorption of carnosine has previously been reported.

In order to achieve the desired cardiotonic effect, carnosine should be administered at appropriate intervals, for example, every 4 to 6 hours. The appropriate interval in a particular case would, of course, depend on the age, weight and condition of the patient. As used herein, the term "patient" includes both humans and animals.

The following examples are provided to describe the invention in further detail. These examples are intended to illustrate and not to limit the invention.

EXAMPLE I

Determination of Cardiac Contractile Function

The effect of carnosine on cardiac function was studied in the isolated rat heart. Male Sprague-Dawley rats were sacrificed with an overdose of pentobarbital (100 mg/kg intraperitoneally) and placed in a Langendorff apparatus within 2–3 minutes. Retrograde aortic perfusion was maintained at a constant pressure of 65 cm of $H_2O$ with oxygenated buffer (95% oxygen, 5% $CO_2$, pH 7.4, 36° C.). The composition of the buffer was: glucose 5.5 mmol/l-NaCl 154 mmol/l, KCl 4.5 mmol/l, $CaCl_2$ 1 mmol/l, $K_2HPO_4$ 1.2 mmol/l, $MgSO_4$ 1.2 mmol/l. Two needle catheters were also placed into the left ventricle. One catheter was perfused with the oxygenated buffer and used to maintain left ventricular diastolic filling pressures (i.e., preload) at approximately 40 mm Hg. The second catheter was attached to a pressure transducer and used to measure left ventricular pressure over time and heart rate. The volume of blood ejected per heart beat (i.e., stroke volume) was approximated by the area under the pressure-time curve (stroke volume=area under the pressure-time curve in mm Hg×sec). Cardiac output was approximated by multiplying stroke volume by heart rate (beats per minute).

The hearts were allowed to stabilize for 20 minutes prior to carnosine administration. Seven control hearts were evaluated for stability over a 20 minute period, during which ventricular pressure and stroke volume remained relatively stable, whereas heart rate and cardiac output decreased over time.

Carnosine (obtained from Sigma Chemical, St. Louis, Mo.) was administered by injection of 1 ml into the aortic cannula, in increasing dosages of 1, 10 and 100 mg/ml. The hearts were allowed to return to baseline between successive dosages. The effect of carnosine on cardiac function at these various dosages is reported in Tables 1–3 below. As can be seen from the data in Tables 1–3, carnosine significantly increased stroke volume and cardiac output at the 10 and 100 mg doses in a dose dependent manner. The peak effect occurred 1 minute following bolus injection of carnosine via the aortic route. Stroke volume and cardiac output returned toward baseline 4 minutes following injection. Cardiac output increased 155% following 10 mg carnosine and 308% after 100 mg carnosine dosages. Carnosine also significantly increased heart rate and ventricular pressures at the 100 mg dose.

TABLE 1

Effect of Carnosine (1 mg) on Cardiac Function (n = 4)

| PARAMETER | BASELINE | 1 MIN | 2 MIN | 4 MIN |
| --- | --- | --- | --- | --- |
| Pressure (mmHG) | | | | |
| Systolic | 60 ± 11 | 62 ± 10 | 61 ± 10 | 61 ± 10 |
| Heart Rate (beats/min) | 76 ± 14 | 78 ± 14 | 76 ± 14 | 76 ± 14 |
| Stroke Volume | 11.4 ± 7.6 | 12.1 ± 7.8 | 12.4 ± 8.5 | 12.9 ± 9.1 |
| Cardiac Output | 964 ± 700 | 1021 ± 719 | 1055 ± 782 | 1108 ± 840 |
| (percent) | (100%) | (106%) | (109%) | (115%) |

TABLE 2

Effect of Carnosine (10 mg) on Cardiac Function (n = 4)

| PARAMETER | BASELINE | 1 MIN | 2 MIN | 4 MIN |
| --- | --- | --- | --- | --- |
| Pressure (mmHG) | | | | |
| Systolic | 60 ± 10 | 66 ± 9 | 65 ± 9 | 61 ± 9 |
| Diastolic | 40 ± 14 | 38 ± 15 | 39 ± 15 | 39 ± 15 |
| Heart Rate (beats/min) | 75 ± 10 | 94 ± 15 | 84 ± 11 | 81 ± 12 |
| Stroke Volume | 12.8 ± 8.9 | 16.3 ± 8.5* | 15.5 ± 8.5* | 13.9 ± 8.9 |
| Cardiac Output | 999 ± 703 | 1544 ± 758* | 1355 ± 785* | 1200 ± 797 |
| (percent) | (100%) | (155%) | (136%) | (120%) |

$p < 0.05$ compared to baseline

TABLE 3

Effect of Carnosine (100 mg) on Cardiac Function (n = 6)

| PARAMETER | BASELINE | 1 MIN | 2 MIN | 4 MIN |
| --- | --- | --- | --- | --- |
| Pressure (mmHG) | | | | |
| Systolic | 54 ± 5 | 82 ± 7* | 72 ± 9 | 71 ± 8 |
| Diastolic | 31 ± 4 | 30 ± 4 | 26 ± 3 | 41 ± 4 |
| Heart Rate (beats/min) | 78 ± 7 | 103 ± 6* | 105 ± 6* | 80 ± 7 |
| Stroke Volume | 16.3 ± 5 | 41.5 ± 10.8* | 33.5 ± 12.0 | 21.3 ± 6.0 |
| Cardiac Output | 1327 ± 482 | 4090 ± 1019* | 3457 ± 1217* | 1691 ± 477 |
| (percent) | (100%) | (308%) | (260%) | (127%) |

$p < 0.05$ compared to baseline

These data indicate that carnosine improves cardiac function in isolated rat hearts. Carnosine improved ventricular pressure generation and increased heart rate, stroke volume and cardiac output. These cardiotonic actions were dose dependent. The increase in heart rate was small (27 beats/min) compared to the increase in stroke volume and cardiac output (approximately 250–300%).

A. Cardiotonic Effect of Carnosine Compared With That of Known β-Adrenergic Receptor Agonists The cardiotonic effects produced by carnosine were compared to those produced by epinephrine (100 mcg/ml) and isoproterenol (10 mcg/ml). Following essentially the same protocol as described in the immediately preceding example, known cardiotonic agents were administered in a volume of 1 ml. These included maximum tolerated doses of epinephrine and isoproterenol in the isolated heart, since higher doses routinely cause ventricular fibrillation.

The results of this comparison are shown in Tables 4 and 5, below. Epinephrine was found to significantly increase heart rate (46%) at 4 minutes, but produced no significant change in ventricular pressure, stroke volume, or cardiac output. Stroke volume tended to decrease following administration of epinephrine. Isoproterenol significantly increased ventricular systolic pressure and decreased ventricular diastolic pressure. Heart rate increased from 110±14 to 151±29 beats/min. Stroke volume and cardiac output increased 2.3 and 2.6 fold, respectively. Compared with isoproterenol, carnosine (100 mg) produced a greater percentage increase in cardiac output (308% vs 262%) for similar increases in stroke volume (255% vs 234%).

heart demonstrate coronary artery vasoconstriction with epinephrine, but not with carnosine.

These data indicate that carnosine's cardiotonic effects are superior to those of epinephrine and isoproterenol. The latter two drugs both produced significant tachycardia, which limited the dose which could be administered. Moreover, both drugs produced ventricular fibrillation in a number of the isolated hearts. On the other hand, ventricular fibrillation did not occur with carnosine. Thus, carnosine appears to produce its cardiotonic effect without causing significant cardiac dysrhythmias.

B. Assessment of Structure-Function Relationship

To determine whether the cardiotonic effects of carnosine (N-β-Alanyl-L-histidine) were structurally specific, a series of structure-function experiments were performed using the isolated rat heart. The experiments involved evaluation of the cardiac effects of β-alanine (50 mg/ml) plus histidine (50 mg/ml), β-Alanyl-phenylalanine (100 mg/ml), N-Acetyl-histidine (100 mg/ml) and β-Alanyl-glycine (100 mg/ml).

The results of these experiments are set forth in Table 6, below. None of the agents compared with carnosine in this experiment produced significant increases in ventricular pressure, heart rate, stroke volume or cardiac output. These data clearly indicate that carnosine's cardiotonic activity is specific to its structure.

TABLE 4

| | Cardiac Effects of Epinephrine (100 mcg), n = 4 | | | |
|---|---|---|---|---|
| PARAMETER | BASELINE | 1 MIN | 2 MIN | 4 MIN |
| Pressure (mmHG) | | | | |
| Systolic | 58 ± 4 | 64 ± 2 | 62 ± 3 | 61 ± 3 |
| Diastolic | 29 ± 5 | 28 ± 4 | 29 ± 5 | 32 ± 7 |
| Heart Rate (beats/min) | 100 ± 24 | 135 ± 35 | 143 ± 34 | 146 ± 41* |
| Stroke Volume | 19.4 ± 8.6 | 18.4 ± 5.9 | 15.7 ± 5.0 | 15.4 ± 6.2 |
| Cardiac Output | 1713 ± 507 | 1963 ± 233 | 1801 ± 249 | 1632 ± 309 |
| (percent) | (100%) | (115%) | (105%) | (95%) |

$p < 0.05$ compared to baseline

TABLE 5

| | Cardiac Effects of Isoproterenol (10 mcg), n = 8 | | | |
|---|---|---|---|---|
| PARAMETER | BASELINE | 1 MIN | 2 MIN | 4 MIN |
| Pressure (mmHG) | | | | |
| Systolic | 42 ± 5 | 69 ± 6* | 72 ± 5* | 66 ± 6* |
| Diastolic | 23 ± 4 | 18 ± 3* | 18 ± 3* | 21 ± 3 |
| Heart Rate (beats/min) | 110 ± 14 | 126 ± 14 | 136 ± 11 | 151 ± 29 |
| Stroke Volume | 8.8 ± 1.8 | 20.6 ± 4.3* | 20.5 ± 3.4* | 17.0 ± 3.3 |
| Cardiac output | 1024 ± 236 | 2436 ± 435* | 2680 ± 393* | 2253 ± 448* |
| (percent) | (100%) | (238%) | (262%) | (220%) |

*$p < 0.05$ compared to baseline

The dose of epinephrine was also limited by coronary artery vasoconstriction (an α-adrenergic receptor effect). Preliminary studies of coronary blood flow in the isolated rat

TABLE 6

Structure-Function Relationships

| AGENT | SYS | DIA | HR | SV | CO |
|---|---|---|---|---|---|
| CARN, n = 6 | | | | | |
| BASE | 54 ± 5 | 31 ± 4 | 78 ± 7 | 16.3 ± 5 | 1327 ± 482 |
| MAX (1 min) | 82 ± 7* | 30 ± 4 | 103 ± 6 | 41.5 ± 10.8* | 4090 ± 1019* |
| Ala—Gly, n = 3 | | | | | |
| BASE | 58 ± 9 | 41 ± 2 | 60 ± 8 | 14.1 ± 8.0 | 909 ± 588 |
| MAX (4 min) | 63 ± 10 | 43 ± 4 | 60 ± 6 | 16.3 ± 9.0 | 1027 ± 546 |
| N—Ac—His, n = 4 | | | | | |
| BASE | 52 ± 8 | 34 ± 3 | 69 ± 7 | 15.4 ± 10.3 | 1007 ± 665 |
| MAX (1 min) | 60 ± 12 | 42 ± 8 | 93 ± 12 | 16.2 ± 11.6 | 1674 ± 1312 |
| Ala—Phe, n = 3 | | | | | |
| BASE | 49 ± 6 | 33 ± 3 | 78 ± 17 | 11.3 ± 5.0 | 743 ± 178 |
| MAX (1 min) | 52 ± 8 | 33 ± 9 | 88 ± 22 | 11.8 ± 7.3 | 971 ± 571 |
| Ala = His, n = 3 | | | | | |
| BASE | 73 ± 8 | 46 ± 10 | 122 ± 24 | 19.7 ± 8.5 | 1994 ± 440 |
| MAX (2 min) | 75 ± 6 | 43 ± 9 | 120 ± 20 | 22.3 ± 9.9 | 2291 ± 583 |

*p<0.05 compared to BASE
SYS=Systolic pressure (mmHG)
DIA=Diastolic pressure (mmHG)
HR=Heart Rate (beats/min)
SV=Stroke Volume
CO=Cardiac Output
MAX=Values for maximal increase in CO (studied at 1,2 and 4 min)
CARN=Carnosine (100 mg), Ala-Gly=beta-alanine-glycine (100 mg), N-Ac-His=N-acetyl-histidine (100 mg), Ala-Phe=beta-alanine-phenylalanine (100 mg), Ala+His=beta-alanine (50 mg) plus histidine (50 mg)

C. Assessment of Whether Carnosine Produces Its Cardiotonic Action Via the β-Adrenergic Receptor Because most cardiac stimulating agents produce their intracellular effects through the β-adrenergic receptor, an experiment was undertaken to determine whether carnosine produced its cardiotonic action in this way. To this end, carnosine's cardiotonic effect was evaluated following β-adrenergic blockage with propranolol. Propranolol was administered slowly until heart rate decreased by 50%. Dosages to achieve the desired effect ranged from 0.3–1.0 mg.

Propranolol results in a significant decrease in ventricular systolic pressure, heart rate, stroke volume and cardiac output, as the data in Table 7 indicate. These decreases were promptly reversed upon administration of carnosine.

TABLE 7

Cardiac Effects of Carnosine (100 mg) with Beta-Adrenergic Receptor Blockade (n = 6)

| PARAMETER | BASELINE | PRO-PRANOLOL | PROP + CARN |
|---|---|---|---|
| Pressure (mmHG) | | | |
| Systolic | 60 ± 4 | 45 ± 4* | 63 ± 3 |
| Diastolic | 30 ± 4 | 35 ± 5 | 30 ± 4 |
| Heart Rate (beats/min) | 100 ± 9 | 36 ± 8* | 92 ± 8 |
| Stroke Volume | 20.3 ± 4.6 | 4.5 ± 1.5* | 28.5 ± 4.7 |
| Cardiac Output | 1875 ± 368 | 207 ± 86* | 2535 ± 436 |

TABLE 7-continued

Cardiac Effects of Carnosine (100 mg) with Beta-Adrenergic Receptor Blockade (n = 6)

| PARAMETER | BASELINE | PRO-PRANOLOL | PROP + CARN |
|---|---|---|---|
| (percent) | (100%) | (11%*) | (135%) |

*p < 0.05 compared to baseline
PROP = propranolol, CARN = carnosine

Since carnosine's cardiotonic action was not blocked by propranolol such activity appears to be independent of the β-adrenergic receptor.

In separate experiments, epinephrine (100 mcg) failed to reverse the changes in ventricular pressure, heart rate, stroke volume and cardiac output produced by the same dose of propranolol, indicating adequate β-adrenergic receptor blockade.

D. Assessment of Whether Carnosine Produces its Cardiotonic Effect via the Histamine-2 Receptor Histamine, a possible metabolite of carnosine, is known to stimulate cardiac contractility through the histamine-2 receptor. Accordingly, experiments were conducted to determine whether carnosine produces its cardiotonic effect via the H2 receptor. To this end, the cardiotonic action of carnosine was evaluated following H2 receptor blockade with cimetidine (1.5 mg). This dose of cimetidine produced significant myocardial depression (70% decrease in estimated stroke volume and blocked the effect of histamine (50 mg/ml) on the heart).

H2 receptor blockade with cimetidine significantly decreased stroke volume and cardiac output, without altering heart rate, as the data in Table 8, below, indicate. Carnosine promptly reversed cimetidine's depressant effects and increased stroke volume and cardiac output significantly above baseline values. These results show that carnosine actions are independent of the H2 receptor.

TABLE 8

Cardiac Effects of Carnosine (CARN; 100 mg)
with H2 Receptor Blockade with Cimetidine
(CIMET), n = 4

| PARAMETER | BASELINE | CIMET | CIMET + CARN |
|---|---|---|---|
| Pressure (mmHG) | | | |
| Systolic | 63 ± 6 | 49 ± 9 | 78 ± 9 |
| Diastolic | 37 ± 10 | 39 ± 11 | 34 ± 7 |
| Heart Rate (beats/ min) | 138 ± 11 | 140 ± 13 | 130 ± 9 |
| Stroke Volume | 12.9 ± 2.4 | 4.1 ± 1.0* | 25.8 ± 7.9* |
| Cardiac Output | 1724 ± 277 | 543 ± 142* | 3328 ± 945* |
| (percent) | (100%) | (31%*) | (193%) |

*p < 0.05 compared to baseline

EXAMPLE II

Measurement of Intracellular Cyclic Adenosine Monophosphate

Most cardiac stimulating agents produce their intracellular effects by elevating cytosolic levels of cAMP. These agents include beta-adrenergic receptor stimulants (i.e., epinephrine, isoproterenol, dobutamine, dopamine), phosphodiesterase inhibitors (i.e., amrinone, milrinone), and glucagon. This experiment was conducted to determine whether carnosine elevated cAMP.

Sprague-Dawley rats (300–400 g) were overdosed with sodium pentobarbital (100 mg/kg intraperitoneally) and the heart extracted. Tissue was removed from the ventricles and cut into small pieces (0.5 mm). The small pieces were placed into oxygenated buffer (95% oxygen, 5% carbon dioxide, pH 7.4, NaCl 154 mmol/l, $MgCl_2$, 1.2 mmol/l, $CaCl_2$ 1 mmol/l, KCl 4 mmol/l) containing trypsin and stirred for 20 minutes at 37° C. The myocardial cell suspension was filtered through cheese cloth and the filtered cells used in subsequent experiments.

Myocardial cell suspensions (0.5 ml) were stimulated with 20 microliters of saline (Control), carnosine 1 mg/ml (CAR-1), carnosine 10 mg/ml (CAR- 10), carnosine 100 mg/ml (CAR-100), epinephrine (EPI; $10^{-4}$M), and forskolin (FORK; $10^{-2}$M). Epinephrine stimulates cAMP production via the beta-adrenergic receptor and forskolin stimulates cAMP production directly via adenyl cyclase activation.

Following a ten minute stimulation period, reactions were stopped with perchloric acid. Perchlorate lysed cells were centrifuged, the supernatant adjusted to pH 7, and 100 microliters of supernatant was used in the assay for cAMP (by radioimmunoassay).

As can be seen from the data in Table 9, below, there was no significant change in cAMP production at the 1 mg/ml and 10 mg/ml carnosine doses. The 100 mg/ml carnosine dose decreased cAMP production below baseline levels. Both epinephrine and forskolin significantly increased cAMP production.

TABLE 9

Effect of Carnosine on Myocyte CAMP (n = 9)

| | cAMP Level (pg/tube) |
|---|---|
| BASELINE | 0.62 ± 0.05 |
| Carnosine, 1 mg/ml | 0.76 ± 0.11 |
| Carnosine, 10 mg/ml | 0.70 ± 0.08 |
| Carnosine, 100 mg/ml | 0.25 ± 0.05* |

TABLE 9-continued

Effect of Carnosine on Myocyte CAMP (n = 9)

| | cAMP Level (pg/tube) |
|---|---|
| Epinephrine, $10^{-4}$M | 1.13 ± 0.14* |
| Forskolin, $10^{-2}$M | 3.54 ± 0.48* |

*p < 0.05 compared to BASELINE

Increased cardiac contractility despite lowering of intracellular cAMP levels is unique to the cariovascular agonist of this invention.

EXAMPLE III

Measurement of Myocyte Free Intracellular Calcium

Myocytes were isolated as in Example II. Free intracellular calcium concentrations, [Ca], were measured using the fluorescent dye, fura-2, according to established procedures. See, for example, G. Grynkiewicz et al., J. Biol. Chem., 260:3440–50 (1985). Fura-2/AM, dissolved in dimethyl sulfoxide, was added to the myocardial cell suspension at a concentration of 3 micromoles/l. The cells were incubated at 37° C. for 30 minutes with continuous stirring. Cells were collected by centrifugation and washed twice in buffer (NaCl 154 mmol/l, $CaCl_2$, 1 mmol/l). After the final wash, myocytes were resuspended in buffer and used for fluorescence measurements. Greater than 95% of the cells are viable by trypan blue exclusion.

Fluorescence measurements were performed in an SLM 8000C spectrofluorometer (SLM Instruments, Urbana, Ill.) at constant temperature (25° C.) and equipped with a magnetic stirrer. Excitation wavelengths were 340 nm and 380 nm. Emission wavelength was 510 nm. Emission readings using alternating 340 nm and 380 nm excitation wavelengths were plotted as the 340/380 ratio. Cells were centrifuged and resuspended immediately prior to measurement to avoid contribution from extracellular fura-2 fluorescence.

[Ca] was calculated using standard methods (see Grynkiewicz et al., supra):

$$[Ca]=Kd\ \{(R-Rmin)/(Rmax-R)\}(SF2/SB2)$$

where, the dissociation constant (Kd) of the fura-2 complex for calcium is 224 nM, R represents the measured 340/380 fluorescence ratio from the myocyte suspension, Rmin represents the minimum fluorescence ratio obtained by adding EDTA after disrupting the cells with digitonin, Rmax represents the maximum fluorescence ratio obtained by adding 1M CaCl2 after disrupting the cells with digitonin, SF2 is the fluorescence of free fura-2 dye at 510 nm, and SB2 represents the fluorescence of calcium bound dye at 510 nm.

[Ca] was measured in the cell suspensions (average of 30 measurements over 1 minute). Following a baseline period the cell suspensions were stimulated with carnosine (100 mg/ml). Maximum increases in [Ca] were achieved by two minutes. Carnosine added to myocyte suspensions lacking fura-2 produced no alteration in the 340/380 fluorescence ratio. BAYK, a calcium channel agonist, was used as a positive control.

Carnosine (100 mg/ml) increased free intracellular calcium levels in isolated rat myocytes from 178 to 275 nmoles/l, as reported in Table 10. The increase in free intracellular calcium was similar to that produced by the slow calcium channel agonist BAYK.

TABLE 10

Effect of Carnosine (100 mg/ml) on Myocyte
Free Intracellular Calcium Levels (n = 4)

|  | Free Intracellular Calcium (nmoles/l) |
|---|---|
| BASELINE | 178 ± 6 |
| CARNOSINE | 275 ± 17* |
| BAYK | 313 ± 33* | p < 0.05 compared to BASELINE

As the data in Table 10 indicate, carnosine was found to increase free intracellular calcium levels in myocytes. This effect on free intracellular calcium may explain its cardiotonic effect. The effect on intracellular calcium appears to be specific for cardiac muscle since carnosine did not cause vasoconstriction of smooth muscle in the coronary arteries.

EXAMPLE IV

In Vivo Blood Pressure Effects

Carnosine was administered intravenously to six intact rats and blood pressure and heart rate was monitored. Blood pressure increased minimally (approximately 5–10 mm Hg) and heart rate remained substantially unchanged. These results suggest that carnosine is not a systemic vasoconstrictor. Thus, carnosine's cardiotonic actions are unique and different from existing therapeutic agents. See Table 11, below.

TABLE 11

Properties of Cardiotonic Agents

| PARAMETER | CARN | ISOP | EPI | DOB | DOP | AMR | DIG |
|---|---|---|---|---|---|---|---|
| Chronotropy | + | +++ | ++ | ++ | ++ | + | − |
| Inotropy | +++ | ++ | ++ | ++ | ++ | + | + |
| Vasoconstrict | − | − | ++ | − | + | − | − |
| Dysrhythmias | − | +++ | ++ | ++ | ++ | + | + |
| Increase cAMP | − | +++ | +++ | +++ | ++ | + | − |
| Increase [Ca] | + | − | − | − | − | − | + |
| Blocked by: | | | | | | | |
| Propranolol | − | + | + | + | + | − | − |
| Cimetidine | − | − | − | − | − | − | − |

+ = Increase, − = no effect
CARN = carnosine, ISOP = isoproterenol, EPI = epinephrine, DOB = dobutamine, DOP = dopamine, AMR = amrinone, DIG = digoxin

EXAMPLE V

Synergy with Beta-Adrenergic Receptor Agonists

Because carnosine lowered cAMP levels, an experiment was undertaken to determine whether it would exhibit synergy with a beta-receptor agonist (which increases cAMP levels). In preliminary studies, it has been found that isoproterenol plus carnosine improves cardiac function to a greater extent than the sum of their individual effects. Thus, it appears that carnosine has a synergistic interaction with beta-adrenergic receptor agonists.

EXAMPLE VI

Beta-adrenergic receptors are frequently downregulated in chronic stress states such as sepsis. Beta-agonists work poorly in these situations. An experiment was conducted involving administration of a cardiotonic effective amount of carnosine to 3 animals (Sprague-Dawley rats) with chronic peritoneal abscesses (produced by cecal-ligation). Carnosine's cardiotonic effect was not impaired in these animals.

EXAMPLE VII

Four isolated hearts were studied over 2 hour periods. Repeated injections of carnosine produced similar effects on the hearts and no evidence of tolerance was apparent in these experiments. We have also administered carnosine intravenously to 6 animals over 6 hour time periods. These animals were allowed to recover and none demonstrated ill effects after 5 days of observation.

The data reported in the foregoing tables are presented as mean±SEM. Differences between groups were analyzed by analysis of variance and Tukey's multiple comparison test. P<0.05 was considered significant.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the amended claims.

What is claimed is:

1. A method of producing a cardiotonic effect in a patient in need thereof, which comprises administering to said patient the compound carnosine or a pharmaceutically acceptable salt thereof in an amount effective to produce said cardiotonic effect.

2. A method as claimed in claim 1 wherein said compound is administered in unit dosage form containing from about 0.01 to about 0.4 grams of said compound per kilogram of patient body weight per day.

3. A method as claimed in claim 2, wherein said unit dosage includes a biologically compatible excipient.

4. A method as claimed in claim 1, wherein said compound is administered parenterally.

5. A method as claimed in claim 4, wherein said compound is administered intravenously.

6. A method as claimed in claim 4, wherein said compound is administered intraperitoneally.

7. A method as claimed in claim 4, wherein said compound is administered intramuscularly.

8. A method as claimed in claim 4, wherein said compound is administered subcutaneously.

9. A method as claimed in claim 4, wherein said compound is administered transdermally.

10. A method as claimed in claim 1, wherein said compound is administered orally.

11. A method as claimed in claim 1, wherein said compound is administered in conjunction with an amount of beta-receptor agonist sufficient to produce a therapeutically effective increase in myocardial cAMP levels.

12. A method as claimed in claim 1, wherein said compound is administered in conjunction with an amount of phosphodiesterase inhibitor sufficient to produce a therapeutically effective increase in myocardial cAMP levels.

* * * * *